United States Patent
Cristau et al.

(10) Patent No.: US 9,439,426 B2
(45) Date of Patent: Sep. 13, 2016

(54) ACTIVE COMPOUND COMBINATIONS COMPRISING CARBOXAMIDE DERIVATIVES AND A BIOLOGICAL CONTROL AGENT

(71) Applicant: BAYER CROPSCIENCE AG, Monheim (DE)

(72) Inventors: Pierre Cristau, Lyons (FR); Peter Dahmen, Neuss (DE)

(73) Assignee: BAYER CROPSCIENCE AG (DE)

( * ) Notice: Subject to any disclaimer, the term of this patent is extended or adjusted under 35 U.S.C. 154(b) by 0 days.

(21) Appl. No.: 14/435,422

(22) PCT Filed: Oct. 17, 2013

(86) PCT No.: PCT/EP2013/071735
§ 371 (c)(1),
(2) Date: Apr. 13, 2015

(87) PCT Pub. No.: WO2014/060521
PCT Pub. Date: Apr. 24, 2014

(65) Prior Publication Data
US 2015/0264928 A1    Sep. 24, 2015

Related U.S. Application Data

(60) Provisional application No. 61/730,289, filed on Nov. 27, 2012.

(30) Foreign Application Priority Data

Oct. 19, 2012 (EP) .................................... 12356023

(51) Int. Cl.
*A01N 25/26* (2006.01)
*A01N 63/00* (2006.01)
*A01N 43/56* (2006.01)

(52) U.S. Cl.
CPC .............. *A01N 43/56* (2013.01); *A01N 63/00* (2013.01)

(58) Field of Classification Search
None
See application file for complete search history.

(56) References Cited

U.S. PATENT DOCUMENTS

| | | | |
|---|---|---|---|
| 2012/0065164 A1 | 3/2012 | Bartels et al. | 514/63 |
| 2014/0038823 A1 | 2/2014 | Dahmen et al. | 504/103 |
| 2014/0051576 A1 | 2/2014 | Dahmen et al. | 504/116.1 |
| 2015/0245610 A1 | 9/2015 | Cristau et al. | |
| 2015/0250176 A1 | 9/2015 | Cristau et al. | |
| 2015/0259294 A1 | 9/2015 | Cristau et al. | |
| 2015/0264927 A1 | 9/2015 | Cristau et al. | |

FOREIGN PATENT DOCUMENTS

| | | | |
|---|---|---|---|
| EP | 2251331 A1 | | 11/2010 |
| WO | WO 2009037242 | * | 3/2009 |
| WO | WO 2010/130767 | | 11/2010 |
| WO | WO 2012/143125 | | 10/2012 |
| WO | WO 2012/143127 | | 10/2012 |
| WO | WO 2014/060502 A1 | | 4/2014 |
| WO | WO 2014/060518 A1 | | 4/2014 |
| WO | WO 2014/060519 A1 | | 4/2014 |
| WO | WO 2014/060520 A1 | | 4/2014 |

OTHER PUBLICATIONS

International Search Report issued Jan. 3, 2014 in corresponding International Application No. PCT/EP2013/071735.

* cited by examiner

*Primary Examiner* — Alton Pryor
(74) *Attorney, Agent, or Firm* — Ostrolenk Faber LLP

(57) ABSTRACT

The present invention relates to active compound combinations, in particular within a composition, which comprises (A)) a N-cyclopropyl-N-[substituted-benzyl]-3-(difluoromethyl)-5-fluoro-1-methyl-1H-pyrazole-4-carboxamide or thiocarboxamide derivative and (B) a biological control agent. Moreover, the invention relates to a method for curatively or preventively controlling the phytopathogenic fungi of plants or crops, to the use of a combination according to the invention for the treatment of seed, to a method for protecting a seed and not at least to the treated seed.

19 Claims, No Drawings

ACTIVE COMPOUND COMBINATIONS COMPRISING CARBOXAMIDE DERIVATIVES AND A BIOLOGICAL CONTROL AGENT

CROSS-REFERENCE TO RELATED APPLICATION(S)

The present application is a 35 U.S.C. §371 national phase conversion of PCT/EP2013/071735 filed on Oct. 17, 2013, which claims priority of European Application No. 12356023.7 filed on Oct. 19, 2012 and U.S. Provisional Application No. 61/730,289 filed on Nov. 27, 2012. Applicants claim priority to each of the foregoing applications. The PCT International Application was published in the English language.

The present invention relates to active compound combinations, in particular within a composition, which comprises (A)) a N-cyclopropyl-N-[substituted-benzyl]-3-(difluoromethyl)-5-fluoro-1-methyl-1H-pyrazole-4-carboxamide or thiocarboxamide derivative and (B) a biological control agent. Moreover, the invention relates to a method for curatively or preventively controlling the phytopathogenic fungi of plants or crops, to the use of a combination according to the invention for the treatment of seed, to a method for protecting a seed and not at least to the treated seed.

N-cyclopropyl-N-[substituted-benzyl]-carboxamides or thiocarboxamides, their preparation from commercially available materials and their use as fungicides are disclosed in WO2007/087906, WO2009/016220, WO2010/130767 and EP2251331. N-cyclopropyl-N-[substituted-benzyl]-3-(difluoromethyl)-5-fluoro-1-methyl-1H-pyrazole-4-carboxamide or thiocarboxamide derivatives as such are already known. It is also known that these compounds can be used as fungicides and mixed with other fungicides or insecticides (cf. patent applications PCT/EP2012/001676 and PCT/EP2012/001674).

Since the environmental and economic requirements imposed on modern-day crop protection compositions are continually increasing, with regard, for example, to the spectrum of action, toxicity, selectivity, application rate, formation of residues, and favorable preparation ability, and since, furthermore, there may be problems, for example, with resistances, a constant task is to develop new compositions, in particular fungicidal agents, which in some areas at least help to fulfill the abovementioned requirements. The present invention provides active compound combinations/compositions which in some aspects at least achieve the stated objective.

It has now been found, surprisingly, that the combinations according to the invention not only bring about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and/or of the component (B) are lowered whilst the action remains equally good. Secondly, the combination still achieves a high degree of phytopathogen control even where the two individual compounds have become totally ineffective in such a low application rate range. This allows, on the one hand, a substantial broadening of the spectrum of phytopathogens that can be controlled and, on the other hand, increased safety in use.

In addition to the fungicidal synergistic activity, the active compound combinations according to the invention have further surprising properties which, in a wider sense, may also be called synergistic, such as, for example: broadening of the activity spectrum to other phytopathogens, for example to resistant strains of plant diseases; lower application rates of the active compounds; sufficient control of pests with the aid of the active compound combinations according to the invention even at application rates where the individual compounds show no or virtually no activity; advantageous behavior during formulation or during use, for example during grinding, sieving, emulsifying, dissolving or dispensing; improved storage stability and light stability; advantageous residue formation; improved toxicological or ecotoxicological behavior; improved properties of the plant, for example better growth, increased harvest yields, a better developed root system, a larger leaf area, greener leaves, stronger shoots, less seed required, lower phytotoxicity, mobilization of the defense system of the plant, good compatibility with plants. Thus, the use of the active compound combinations or compositions according to the invention contributes considerably to keeping young cereal stands healthy, which increases, for example, the winter survival of the cereal seed treated, and also safeguards quality and yield. Moreover, the active compound combinations according to the invention may contribute to enhanced systemic action. Even if the individual compounds of the combination have no sufficient systemic properties, the active compound combinations according to the invention may still have this property. In a similar manner, the active compound combinations according to the invention may result in higher persistency of the fungicidal action.

Accordingly, the present invention provides a combination comprising:
(A) at least one derivative of formula (I)

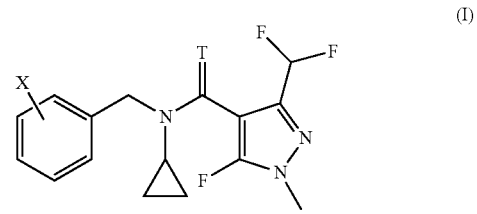

wherein T represents an oxygen or a sulfur atom and X is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl) and 2-ethyl-4,5-dimethyl, or an agrochemically acceptable salt thereof,
and
(B) at least one biological control agent.

Preference is given to combinations comprising at least one compound of the formula (I) selected from the group consisting of:
N-cyclopropyl-3-(difluoromethyl)-5-fluoro-N-(2-isopropylbenzyl)-1-methyl-1H-pyrazole-4-carboxamide (compound A1),
N-cyclopropyl-N-(2-cyclopropylbenzyl)-3-(difluoromethyl)-5-fluoro-1-methyl-1H-pyrazole-4-carboxamide (compound A2), N-(2-tert-butylbenzyl)-N-cyclopropyl-3-(difluoromethyl)-5-fluoro-1-methyl-1H-pyrazole-4-carboxamide (compound A3),
N-(5-chloro-2-ethylbenzyl)-N-cyclopropyl-3-(difluoromethyl)-5-fluoro-1-methyl-1H-pyrazole-4-carboxamide (compound A4),
N-(5-chloro-2-isopropylbenzyl)-N-cyclopropyl-3-(difluoromethyl)-5-fluoro-1-methyl-1H-pyrazole-4-carboxamide (compound A5),
N-cyclopropyl-3-(difluoromethyl)-N-(2-ethyl-5-fluorobenzyl)-5-fluoro-1-methyl-1H-pyrazole-4-carboxamide (compound A6),
N-cyclopropyl-3-(difluoromethyl)-5-fluoro-N-(5-fluoro-2-isopropylbenzyl)-1-methyl-1H-pyrazole-4-carboxamide (compound A7),
N-cyclopropyl-N-(2-cyclopropyl-5-fluorobenzyl)-3-(difluoromethyl)-5-fluoro-1-methyl-1H-pyrazole-4-carboxamide (compound A8),
N-(2-cyclopentyl-5-fluorobenzyl)-N-cyclopropyl-3-(difluoromethyl)-5-fluoro-1-methyl-1H-pyrazole-4-carboxamide (compound A9),
N-cyclopropyl-3-(difluoromethyl)-5-fluoro-N-(2-fluoro-6-isopropylbenzyl)-1-methyl-1H-pyrazole-4-carboxamide (compound A10),
N-cyclopropyl-3-(difluoromethyl)-N-(2-ethyl-5-methylbenzyl)-5-fluoro-1-methyl-1H-pyrazole-4-carboxamide (compound A11),
N-cyclopropyl-3-(difluoromethyl)-5-fluoro-N-(2-isopropyl-5-methylbenzyl)-1-methyl-1H-pyrazole-4-carboxamide (compound A12),
N-cyclopropyl-N-(2-cyclopropyl-5-methylbenzyl)-3-(difluoromethyl)-5-fluoro-1-methyl-1H-pyrazole-4-carboxamide (compound A13),
N-(2-tert-butyl-5-methylbenzyl)-N-cyclopropyl-3-(difluoromethyl)-5-fluoro-1-methyl-1H-pyrazole-4-carboxamide (compound A14),
N-[5-chloro-2-(trifluoromethyl)benzyl]-N-cyclopropyl-3-(difluoromethyl)-5-fluoro-1-methyl-1H-pyrazole-4-carboxamide (compound A15),
N-cyclopropyl-3-(difluoromethyl)-5-fluoro-1-methyl-N-[5-methyl-2-(trifluoromethyl)benzyl]-1H-pyrazole-4-carboxamide (compound A16),
N-[2-chloro-6-(trifluoromethyl)benzyl]-N-cyclopropyl-3-(difluoromethyl)-5-fluoro-1-methyl-1H-pyrazole-4-carboxamide (compound A17),
N-[3-chloro-2-fluoro-6-(trifluoromethyl)benzyl]-N-cyclopropyl-3-(difluoromethyl)-5-fluoro-1-methyl-1H-pyrazole-4-carboxamide (compound A18).
N-cyclopropyl-3-(difluoromethyl)-N-(2-ethyl-4,5-dimethylbenzyl)-5-fluoro-1-methyl-1H-pyrazole-4-carboxamide (compound A19),
and N-cyclopropyl-3-(difluoromethyl)-5-fluoro-N-(2-isopropylbenzyl)-1-methyl-1H-pyrazole-4-carbothio-amide (compound A20).

Biological Control Agents

Biological control agent (or biologic or biological) comprises in particular bacteria, fungi or yeasts, protozoa, viruses, entomopathogenic nematode, inoculants, botanicals and products produced by microorganisms including proteins or secondary metabolites.

According to the invention biological control agents which are summarized under the term "bacteria" include spore-forming, root-colonizing bacteria, or bacteria useful as bioinsecticide, biofungicide or bionematicide. Examples of such bacteria to be used or employed according to the invention are:

(1.1) *Agrobacterium radiobacter* (only named in patents), (1.2) *Bacillus acidocaldarius* (only named in patents), (1.3) *Bacillus acidoterrestris* (only named in patents), (1.4) *Bacillus agri* (only named in patents), (1.5) *Bacillus aizawai* (only named in patents), (1.6) *Bacillus albolactis* (only named in patents), (1.7) *Bacillus alcalophilus* (only named in patents), (1.8) *Bacillus alvei* (only named in patents), (1.9) *Bacillus aminoglucosidicus* (only named in patents), (1.10) *Bacillus aminovorans* (only named in patents), (1.11) *Bacillus amylolyticus* (also known as *Paenibacillus amylolyticus*) (1.12) *Bacillus amyloliquefaciens*, in particular strain IN937a, or strain FZB42 (product known as RhizoVital®), or strain B3, (1.13) *Bacillus aneurinolyticus*, (1.14) *Bacillus atrophaeus*, (1.15) *Bacillus azotoformans* (only named in patents), (1.16) *Bacillus badius* (only named in patents), (1.17) *Bacillus cereus* (synonyms: *Bacillus endorhythmos*, *Bacillus medusa*), in particular spores of *B. cereus* strain CNCM I-1562 (cf. U.S. Pat. No. 6,406,690), (1.18) *Bacillus chitinosporus*, in particular strain AQ746 (Accession No. NRRL B-21618), (1.19) *Bacillus circulans* (1.20) *Bacillus coagulans*, (1.21) *Bacillus fastidiosus* (only named in patents), (1.23) *Bacillus firmus*, in particular strain I-1582 (products known as Bionem, VOTIVO), (1.24) *Bacillus kurstaki* (only named in patents), (1.25) *Bacillus lacticola* (only named in patents), (1.26) *Bacillus lactimorbus* (only named in patents), (1.27) *Bacillus lactis* (only named in patents), (1.28) *Bacillus laterosporus* (also known as *Brevibacillus laterosporus*), (1.29) *Bacillus lautus* (only named in patents), (1.30) *Bacillus lentimorbus*, (1.31) *Bacillus lentos*, (1.32) *Bacillus licheniformis*, (1.33) *Bacillus maroccanus*, (1.34) *Bacillus megaterium* (products known as BioArc), (1.35) *Bacillus metiens*, (1.36) *Bacillus mycoides*, in particular strain AQ726 (Accession No. NRRL B21664) or isolate J (BmJ), (1.37) *Bacillus natto*, (1.38) *Bacillus nematocida*, (1.39) *Bacillus nigrificans*, (1.40) *Bacillus nigrum*, (1.41) *Bacillus pantothenticus*, (1.42) *Bacillus popillae* (products known as Cronox), (1.43) *Bacillus psychrosaccharolyticus* (only named in patents), (1.44) *Bacillus pumilus*, in particular strain GB34 (products known as Yield Shield®) and strain QST2808 (Accession No. NRRL B-30087, products known as Sonata QST 2808®) or strain AQ717 (Accession No. NRRL B21662), (1.45) *Bacillus siamensis* (only named in patents), (1.46) *Bacillus smithii* (only named in patents), (1.47) *Bacillus sphaericus* (products known as VectoLexs®), (1.48) *Bacillus subtilis*, in particular strain GB03 (products known as Kodiak®) and strain QST713/AQ713 (Accession No. NRRL B-21661, products known as Serenade QST 713®, Serenade Soil, Serenade Max, Cease) and strain AQ743 (Accession No. NRRL B-21665) and strain AQ 153 (ATCC accession No. 55614) or *B. subtilis* var. *amyloliquefaciens* strain FZB24 (products known as Taegro®), (1.49) *Bacillus thuringiensis*, in particular *B. thuringiensis* var. *israelensis* (products known as VectoBac®) or *B. thuringiensis* subsp. *aizawai* strain ABTS-1857 (products known as XenTari®), or *B. thuringiensis* subsp. *kurstaki* strain HD-1 (products known as Dipel® ES) or strain BMP 123 or *B. thuringiensis* subsp. *tenebrionis* strain NB 176 (products known as Novodor® FC), or *B. thuringiensis* var. *aegyptii* (products known as Agerin), or *B. thuringiensis* var. *colmeri* (products known as TianBaoBTc), or *B. thuringiensis* var. *darmstadiensis* (products known as Baciturin, Kolepterin), or *B. thuringiensis* var. *dendrolimus* (products known as Dendrobacillin), or *B. thuringiensis* var. *galleriae* ((products known as Enterobactin), or *B. thuringiensis* var. *japonensis* (products known as Buihunter), or *B. thuringiensis* subsp. *morrisoni*, or *B. thuringiensis* var. *san diego*, or *B. thuringiensis* subsp.

*thuringiensis* strain MPPL002, or *B. thuringiensis* var. *thuringiensis* (products known as Bikol), or *B. thuringiensis* var 7216 (products known as Amactic, Pethian), or *B. thuringiensis* var T36 (products known as Cahat) or *B. thuringiensis* strain BD#32 (Accession No. NRRL B-21530) or *B. thuringiensis* strain AQ52 (Accession No. NRRL B-21619), (1.50) *Bacillus uniflagellatus*, (1.51) *Bradyrhizobium japonicum* (Symbiont?, products known as SoySelect), (1.52) *Bacillus* sp. strain AQ175 (ATCC Accession No. 55608), (1.53) *Bacillus* sp. strain AQ177 (ATCC Accession No. 55609), (1.54) *Bacillus* sp. strain AQ178 (ATCC Accession No. 53522), (1.55) Brevibacillus *brevis* (formerly *Bacillus brevis*), in particular strains SS86-3, SS86-4, SS86-5, 2904, (1.56) *Brevibacillus laterosporus* (formerly *Bacillus laterosporus*), in particular strains 64, 1111, 1645, 1647, (1.57) *Chromobacterium subtsugae*, in particular strain PRAA4-1T (products known as Gandevo), (1.58) *Delftia acidovorans*, in particular strain RAY209 (products known as BioBoost®), (1.59) *Lactobacillus acidophilus* (products known as Fruitsan), (1.60) *Lysobacter antibioticus*, in particular strain 13-1 (cf. Biological Control 2008, 45, 288-296), (1.61) *Lysobacter enzymogenes*, in particular strain C3 (cf. J Nematol. 2006 June; 38(2): 233-239), (1.62) *Paenibacillus alvei*, in particular strains III3DT-1A, 1112E, 46C3, 2771 (*Bacillus* genetic stock center, November 2001), (1.63) *Paenibacillus polymyxa*, (1.64) *Paenibacillus popilliae* (formerly *Bacillus popilliae*), (1.65) *Pantoea agglomerans*, (1.66) *Pasteuria penetrans* (formerly *Bacillus penetrans*), products known as *Pasteuria* wettable powder, (1.67) *Pasteuria usgae* (products known as Econem™), (1.68) *Pectobacterium carotovorum* (formerly *Erwinia carotovora*) products known as BioKeeper, (1.69) *Pseudomonas aeruginosa* (products known as Guiticid), (1.70) *Pseudomonas aureofaciens* (products known as Agate-25K), (1.71) *Pseudomonas cepacia* (formerly known as *Burkholderia cepacia*), in particular strains M54 or J82, (1.72) *Pseudomonas chlororaphis*, in particular strain MA 342 (products known as Cedomon), (1.73) *Pseudomonas fluorescens* (products known as Sudozone), (1.74) *Pseudomonas proradix* (products known as Proradix), (1.75) *Pseudomonas putida* (products known as Nematsid, (1.76) *Pseudomonas resinovorans* (products known as Solanacure), (1.77) *Pseudomonas syringae* (products known as Biosave), (1.78) *Rhodococcus globerulus* strain AQ719 (Accession No. NRRL B21663) (1.79) *Serratia entomophila* (products known as invade), (1.80) *Serratia marcescens*, in particular strain SRM (MTCC8708) or strain R35, (1.81) *Streptomyces candidus* (products known as BioAid™), (1.82) *Streptomyces colombiensis* (products known as Mycoside), (1.83) *Streptomyces galbus*, in particular strain K61 (products known as Mycostop®, cf. Crop Protection 2006, 25, 468-475) or strain QST 6047 (Accession No. NRRL B21663), (1.84) *Streptomyces goshikiensis* (products known as Safegro), (1.85) *Streptomyces griseoviridis* (products known as Mycostop®, cf. Microbial db of Canada), (1.86) *Streptomyces lavendulae* (products known as Phytolavin-300), (1.87) *Streptomyces lydicus*, in particular strain WYCD108 (products known as ActinovateSP) or strain WYEC108 (products known as Actino-iron), (1.88) *Streptomyces prasinus* (cf "Prasinons A and B: potent insecticides from *Streptomyces prasinus*" Applied microbiology 1973 November), (1.89) *Streptomyces rimosus* (products known as Rhitovit), (1.90) *Streptomyces saraceticus* (products known as Clanda), (1.91) *Streptomyces venezuelae*, (1.92) *Streptomyces* sp. NRRL B30145 (1.93) *Xanthomonas campestris* (herbicidal activity), (1.94) *Xenorhabdus luminescens*, (1.95) and *Xenorhabdus nematophila*.

According to the invention biological control agents that are summarized under the term "fungi" or "yeasts" are:

(2.1) *Ampelomyces quisqualis*, in particular strain AQ 10 (product known as AQ 10®), (2.2) *Aureobasidium pullulans*, in particular blastospores of strain DSM14940 or blastospores of strain DSM 14941 or mixtures thereof (product known as Blossom Protect®), (2.3) *Aschersonia aleyrodes*, (2.4) *Aspergillus flavus*, in particular strain NRRL 21882 (products known as Afla-Guard®), (2.5) *Arthrobotrys superba* (Corda 1839), (2.6) *Beauveria bassiana*, in particular strain ATCC 74040 (products known as Naturalis®) and strain GHA (products known as Mycotrol, BotaniGard), (2.7) *Beauveria brongniartii* (products known as Beaupro), (2.8) *Candida oleophila*, in particular strain O (products known as Nexy®, Aspire), (2.9) *Chaetomium cupreum* (products known as Ketocin), (2.10) *Cladosporium cladosporioides*, in particular strain H39, (2.11) *Conidiobolus obscurus*, (2.12) *Coniothyrium minitans*, in particular strain CON/M/91-8 (products known as Contans®), (2.13) *Dilophosphora alopecuri* (products known as Twist Fungus®), (2.14) *Entomophthora virulenta* (products known as Vektor), (2.15) *Fusarium oxysporum*, in particular strain Fo47 (non-pathogenic) (products known as Fusaclean), (2.16) *Gliocladium catenulatum*, in particular strain J1446 (products known as Prestop® or Primastop), (2.17) *Hirsutella thompsonii* (products known as Mycohit or ABTEC), (2.18) *Lagenidium giganteum* (products known as Laginex® by AgraQuest, Inc.), (2.19) *Lecanicillium lecanii* (formerly known as *Verticillium lecanii*), in particular conidia of strain KV01 (products known as Mycotal®, Vertalec®), (2.20) *Metarhizium anisopliae*, in particular strain F52 (products known as BIO 1020 or Met52), or M. a. var acridum (products known as Green Muscle), (2.21) *Metarhizium flavoviride*, (2.22) *Metschnikovia fructicola*, in particular the strain NRRL Y-30752 (product known as Shemer®), (2.23) *Microsphaeropsis ochracea* (products known as Microx®), (2.24) *Mucor haemelis* (product known as BioAvard), (2.25) *Muscodor albus*, in particular strain QST 20799 (products known as Arabesque™ or Andante™) and strain 620 (Accession No. NRRL 30547), (2.26) *Muscodor roseus* strain A3-5 (Accession No. NRRL 30548) (2.27) *Myrothecium verrucaria*, in particular strain AARC-0255 (products known as DiTera™), (2.28) *Nomuraea rileyi*, in particular strains SA86101, GU87401, SR86151, CG128 and VA9101 (products known as Kongo®), (2.29) *Ophiostoma piliferum*, in particular strain D97 (products known as Sylvanex), (2.30) *Paecilomyces fumosoroseus* (new: *Isaria fumosorosea*), in particular strain apopka 97 (products known as PreFeRal), (2.31) *Paecilomyces lilacinus*, in particular spores of *P. lilacinus* strain 251 (products known as Bio-Act®, cf. Crop Protection 2008, 27, 352-361), (2.32) *Paecilomyces variotii*, in particular strain Q-09 (products known as Nemaquim), (2.33) *Pandora delphacis*, (2.34) *Penicillium bilaii*, in particular strain ATCC22348 (products known as JumpStart®, PB-50, Provide), (2.35) *Penicillium vermiculatum* (products known as Vermiculen), (2.36) *Phlebiopsis* (=*Phlebia*=*Peniophora*) *gigantea* (products known as Rotstop), (2.37) *Pichia anomala*, in particular strain WRL-076, (2.38) *Pochonia chlamydosporia*, (2.39) *Pseudozyma flocculosa*, in particular strain PF-A22 UL (products known as Sporodex® L), (2.40) *Pythium oligandrum*, in particular strain DV74 (products known as Polyversum), (2.41) *Sporothrix insectorum* (products known as *Sporothrix*), (2.42) *Talaromyces flavus*, (2.43) *Trichoderma album* (products known as Bio-Zeid), (2.44) *Trichoderma asperellum*, in particular strain ICC 012 (products known as Bioten®), (2.45) *Trichoderma atroviride*, in particular strain CNCM 1-1237, (2.46) *Trichoderma gamsii* (formerly *T. virile*), in particular mycelial fragments, conidia & chlamydospores of strain ICC080 (products known as Bioderma), (2.47) *Trichoderma harmatum*, (2.48) *Trichoderma harzianum*, in particular *T. harzianum* T39 (products known as Trichodex®), (2.49) *Trichoderma koningii* (products known as Trikot-S Plus), (2.50) *Trichoderma lignorum* (products known as Mycobac), (2.51) *Trichoderma polysporum*, in particular strain IMI 206039, (2.52) *Trichoderma virens* (formerly *Gliocladium virens*), (products known as Soil-Gard), (2.53) *Tsukamurella paurometabola* (products known as HeberNem®), (2.54) *Ulocladium oudemansii* (products known as Botry-Zen), (2.55) *Verticillium albo-atrum*, in particular strain WCS850, (2.56) *Verticillium chlamydosporium* (products known as Varsha), (2.57) *Verticillium dahliae* (products known as Dutch Trig), and (2.58) *Zoophtora radicans*.

According to the invention biological control agents that are summarized under the term "protozoas" are:

(3.1) *Nosema locustae* (products known as NoloBait), (3.2) *Thelohania solenopsis* and (3.3) *Vairimorpha* spp.

According to the invention biological control agents that are summarized under the term "viruses" are:

(4.1) *Adoxophyes orana* (summer fruit tortrix) granulosis virus (GV), (product known as BIOFA—Capex®), (4.2) *Agrotis segetum* (turnip moth) nuclear polyhedrosis virus (NPV), (4.3) *Anticarsia gemmatalis* (Woolly pyrol moth) mNPV (products known as Polygen), (4.4) *Autographa californica* (Alfalfa Looper) mNPV (products known as VPN80 from Agricola El Sol), (4.5) *Biston suppressaria* (tea looper) NPV, (4.6) *Bombyx mori* (silkworm) NPV, (4.7) *Cryptophlebia leucotreta* (false codling moth) GV (products known as Cryptex), (4.8) *Cydia pomonella* (Codling moth) granulosis virus (GV) (product known as Madex Plus), (4.9) *Dendrolimus punctatus* (Masson pine moth) CPV, (4.10) *Helicoverpa armigera* NPV (product known as AgBiTech—ViVUS Max), (4.11) *Helicoverpa* (previously *Heliothis*) *zea* (corn earworm) NPV (products known as Elcar), (4.12) *Leucoma salicis* (satin moth) NPV, (4.13) *Lymantria dispar* (gypsy moth) NPV (products known as Gypcheck), (4.14) *Neodiprion abietis* (balsam-fir sawfly) NPV (products known as Abietiv), (4.15) *Neodiprion lecontei* (red-headed pinesawfly) NPV (products known as Lecontvirus), (4.16) *Neodiprion sertifer* (Pine sawfly) NPV (products known as Neocheck-S), (4.17) *Orgyia pseudotsugata* (Douglas-fir tussock moth) NPV (products known as Virtuss), (4.18) *Phthorimaea operculella* (tobacco leaf miner) GV (products known as Matapol), (4.19) *Pieris rapae* (small white butterfly) GV, (4.20) *Plutella xylostella* (diamondback moth) GV (products known as Plutec), (4.21) *Spodoptera albula* (gray-streaked armyworm moth) mNPV (products known as VPN 82), (4.22) *Spodoptera exempta* (true armyworm) mNPV (products known as Spodec), (4.23) *Spodoptera exigua* (sugarbeet armyworm) mNPV (products known as Spexit from Andermatt Biocontrol), (4.24) *Spodoptera frugiperda* (fall armyworm) mNPV (products known as Baculovirus VPN), (4.25) *Spodoptera littoralis* (tobacco cutworm) NPV (procucts known as Spodoptrin from NPP Calliope France), and (4.26) *Spodoptera litura* (oriental leafworm moth) NPV (products known as Littovir).

According to the invention biological control agents that are summarized under the term "entomopathogenic nematodes" are:

(5.1) *Abbreviata caucasica*, (5.2) *Acuaria* spp., (5.3) *Agamermis decaudata*, (5.4) *Allantonema* spp., (5.5) *Amphimermis* spp., (5.6) *Beddingia* (=*Deladenus*) *siridicola*, (5.7) *Bovienema* spp., (5.7) *Cameronia* spp., (5.8) *Chitwoodiella ovofilamenta*, (5.9) *Contortylenchus* spp., (5.10) *Culicimennis* spp., (5.11) *Diplotriaena* spp., (5.12) *Empidomermis* spp., (5.13) *Filipjevimermis leipsandra*, (5.14) *Gastromermis* spp., (5.15) *Gongylonema* spp., (5.16) *Gynopoecilia pseudovipara*, (5.17) *Heterorhabditis* spp., in particular *Heterorhabditis bacteriophora* (products known as B-Green), or *Heterorhabditis baujardi*, or *Heterorhabditis heliothidis* (products known as Nematon), or *Heterorhabditis indica*, *Heterorhabditis marelatus*, *Heterorhabditis megidis*, *Heterorhabditis zealandica*, (5.18) *Hexamermis* spp., (5.19) *Hydromermis* spp., (5.20) *Isomenis* spp., (5.21) *Limnomennis* spp., (5.22) *Maupasina weissi*, (5.23) *Mermis nigrescens*, (5.24) *Mesomermis* spp., (5.25) *Neomesomermis* spp., (5.26) *Neoparasitylenchus rugulosi*, (5.27) *Octomyomermis* spp., (5.28) *Parasitaphelenchus* spp., (5.29) *Parasitorhabditis* spp., (5.30) *Parasitylenchus* spp., (5.31) *Perutilimennis culicis*, (5.32) *Phasmarhabditis hermaphrodita*, (5.33) *Physaloptera* spp., (5.34) *Protrellatus* spp., (5.35) *Pterygodematites* spp., (5.36) *Romanomermis* spp., (5.37) *Seuratum cadarachense*, (5.38) *Sphaerulariopsis* spp., (5.39) *Spirura guianensis*, (5.40) *Steinernema* spp. (=*Neoaplectana* spp.), in particular *Steinernema bibionis*, or *Steinernema carpocapsae* (products known as Biocontrol), or *Steinernema feltiae* (=*Neoaplectana carpocapsae*), (products known as Nemasys®), or *Steinernema glaseri* (procucts known as Biotopia), or *Steinernema kraussei* (products known as Larvesure), or *Steinernema riobrave* (products known as Biovector), or *Steinernema scapterisci* (products known as Nematac S), or *Steinernema scarabaei*, or *Steinernema siamkayai*, (5.41) *Strelkovimermis peterseni*, (5.42) *Subulura* spp., (5.43) *Sulphuretylenchus elongatus*, and (5.44) *Tetrameres* spp.

According to the invention biological control agents that are summarized under the term "inoculants" are:

(6.1) *Agrobacterium* spp., (6.2) *Azorhizobium caulinodans*, (6.3) *Azospirillum* spp., (6.4) *Azotobacter* spp., (6.5) *Bradyrhizobium* spp., (6.6) *Burkholderia* spp., in particular *Burkholderia cepacia* (formerly *Pseudomonas cepacia*), (6.7) *Gigaspora* spp., in particular *Gigaspora margarita*, or *Gigaspora monosporum*, (6.8) *Glomus* spp., in particular *Glomus aggregatum*, or *Glomus brasilianum*, or *Glomus clarum*, or *Glomus deserticola*, or *Glomus etunicatum*, or *Glomus intraradices*, or *Glomus monosporus*, or *Glomus mosseae*, (6.9) *Laccaria* spp., in particular *Laccaria bicolor*, or *Laccaria laccata*, (6.10) *Lactobacillus buchneri*, (6.11) *Paraglomus* spp., (6.12) *Pisolithus tinctorus*, (6.13) *Pseudomonas* spp., (6.14) *Rhizobium* spp., in particular *Rhizobium fredii*, or *Rhizobium leguminosarum*, or *Rhizobium loti*, or *Rhizobium meliloti*, or *Rhizobium trifolii*, or *Rhizobium tropici*, (0.6.15) *Rhizopogon* spp., in particular *Rhizopogon amylopogon*, or *Rhizopogon fulvigleba*, or *Rhizopogon luteolus*, or *Rhizopogon tinctorus*, or *Rhizopogon villosullus*, or (0.6.16) *Scleroderma* spp., in particular *Scleroderma cepa*, or *Scleroderma citrinum*, (6.17) *Suillus* spp., in particular *Suillus granulates*, or *Suillus punctatapies* and (6.18) *Streptomyces* spp.

According to the invention biological control agents that are summarized under the term "Botanicals" are:

(7.1) Thymol, extracted e. g. from thyme (*thymus vulgaris*), (7.2) Neem tree (*Azadirachta indica*) oil, and therein Azadirachtin, (7.3) Pyrethrum, an extract made from the dried flower heads of different species of the genus *Tanacetum*, and therein Pyrethrins (the active components of the extract), (7.4) extract of *Cassia nigricans*, (7.5) wood extract of *Quassia amara* (bitterwood), (7.6) Rotenon, an extract from the roots and stems of several tropical and subtropical plant species, especially those belonging to the genera

*Lonchocarpus* and *Derris*, (7.7) extract of *Allium sativum* (garlic), (7.8) *Quillaja* extract, made from the concentrated purified extract of the outer cambium layer of the *Quillaja Saponaria Molina* tree, (7.9) *Sabadilla* (*Sabadilla=Schoenocaulon officinale*) seeds, in particular Veratrin (extracted from the seeds), (7.10) *Ryania*, an extract made from the ground stems of *Ryania speciosa*, in particular Ryanodine (the active component of the extract), (7.11) extract of *Viscum album* (mistletoe), (7.12) extract of *Tanacetum vulgare* (tansy), (7.13) extract of *Artemisia absinthium* (wormwood), (7.14) extract of *Urtica dioica* (stinging nettle), (7.15) extract of *Symphytum officinale* (common comfrey), (7.16) extract of *Tropaeulum majus* (monks cress), (7.17) leaves and bark of *Quercus* (oak tree) (7.18) Yellow mustard powder, (7.19) oil of the seeds of *Chenopodium anthelminticum* (wormseed goosefoot), (7.20) dried leaves of *Dryopteris filix-mas* (male fern), (7.21) bark of *Celastrus angulatus* (Chinese bittersweet), (7.22) extract of *Equisetum arvense* (field horsetail), (7.23) Chitin (7.24 natural extracts or simulated blend of *Chenopodium ambrosioides* (products known as Requiem), (7.25) Saponins of *Chenopodium quinoa* (products known as Heads Up).

According to the invention biological control agents that are "Products produced by microorganisms including proteins or secondary metabolites" are:

(8.1) Harpin (isolated by *Erwinia amylovora*, products known as Harp-N-Tek™, Messenger®, Employ™, Pro-Act™).

Preference is given to the use of compositions comprising a combination of a compound (A1), (A2), (A3), (A4), (A5), (A6), (A7), (A8), (A9), (A10), (A11), (A12), (A13), (A14), (A15), (A16) (A17), (A18), (A19) or (A20) with one or more active compounds from the group of the bacteria, fungi or yeast, protozoas, viruses, entomopathogenic nematodes, inoculants, botanicals or products produced by microorganisms including proteins or secondary metabolites as above described.

In particular this invention is directed to mixtures comprising the compound (A1), (A2), (A3), (A4), (A5), (A6), (A7), (A8), (A9), (A10), (A11), (A12), (A13), (A14), (A15), (A16) (A17), (A18), (A19) or (A20) as compound of formula (I) and at least one compound selected among the list L1 consisting of (1.1), (1.2), (1.3), (1.4), (1.5), (1.6), (1.7), (1.8), (1.9), (1.10), (1.11), (1.12), (1.13), (1.14), (1.15), (1.16), (1.17), (1.18), (1.19), (1.20), (1.21), (1.23), (1.24), (1.25), (1.26), (1.27), (1.28), (1.29), (1.30), (1.31), (1.32), (1.33), (1.34), (1.35), (1.36), (1.37), (1.38), (1.39), (1.40), (1.41), (1.42), (1.43), (1.44), (1.45), (1.46), (1.47), (1.48), (1.49), (1.50), (1.51), (1.52), (1.53), (1.54), (1.55); (1.56), (1.57), (1.58), (1.59), (1.60), (1.61), (1.62), (1.63), (1.64), (1.65), (1.66), (1.67), (1.68), (1.69), (1.70), (1.71), (1.72), (1.73), (1.74), (1.75), (1.76), (1.77), (1.78), (1.79), (1.80), (1.81), (1.82), (1.83), (1.84), (1.85), (1.86), (1.87), (1.88), (1.89), (1.90), (1.91), (1.92), (1.93), (1.94), (1.95), (2.1), (2.2), (2.3), (2.4), (2.5), (2.6), (2.7), (2.8), (2.9), (2.10), (2.11), (2.12), (2.13), (2.14), (2.15), (2.16), (2.17), (2.18), (2.19), (2.20), (2.21), (2.23), (2.24), (2.25), (2.26), (2.27), (2.28), (2.29), (2.30), (2.31), (2.32), (2.33), (2.34), (2.35), (2.36), (2.37), (2.38), (2.39), (2.40), (2.41), (2.42), (2.43), (2.44), (2.45), (2.46), (2.47), (2.48), (2.49), (2.50), (2.51), (2.52), (2.53), (2.54), (2.55); (2.56), (2.57), (2.58), (3.1), (3.2), (3.3), (4.1), (4.2), (4.3), (4.4), (4.5), (4.6), (4.7), (4.8), (4.9), (4.10), (4.11), (4.12), (4.13), (4.14), (4.15), (4.16), (4.17), (4.18), (4.19), (4.20), (4.21), (4.22), (4.23), (4.24), (4.25), (4.26), (5.1), (5.2), (5.3), (5.4), (5.5), (5.6), (5.7), (5.8), (5.9), (5.10), (5.11), (5.12), (5.13), (5.14), (5.15), (5.16), (5.17), (5.18), (5.19), (5.20), (5.21), (5.22), (5.23), (5.24), (5.25), (5.26), (5.27), (5.28), (5.29), (5.30), (5.31), (5.32), (5.33), (5.34), (5.35), (5.36), (5.37), (5.38), (5.39), (5.40), (5.41), (5.42), (5.43), (5.44), (6.1), (6.2), (6.3), (6.4), (6.5), (6.6), (6.7), (6.8), (6.9), (6.10), (6.11), (6.12), (6.13), (6.14), (6.15), (6.16), (6.17), (6.18), (7.1), (7.2), (7.3), (7.4), (7.5), (7.6), (7.7), (7.8), (7.9), (7.10), (7.11), (7.12), (7.13), (7.14), (7.15), (7.16), (7.17), (7.18), (7.19), (7.20), (7.21), (7.22), (7.23), (7.24), (7.25), (8.1).

In a particular embodiment of the invention, the biological control agent used in the active compound combinations and compositions of the invention is chosen among *Bacillus* sp., in particular among *Bacillus pumilus, Bacillus subtilis, Bacillus amyloliquefaciens* and *Bacillus firmus*; Even more in particular among among *Bacillus pumilus, Bacillus subtilis*.

In a particular embodiment of the invention, the biological control agent used in the active compound combinations and compositions of the invention is chosen among:

*Bacillus pumilus*, in particular strain GB34 (products known as Yield Shield®) or strain QST2808 (Accession No. NRRL B-30087, products known as Sonata QST 2808®) or strain AQ717 (Accession No. NRRL B21662), or

*Bacillus subtilis*, in particular strain GB03 (products known as Kodiak®) or strain QST713/AQ713 (Accession No. NRRL B-21661, products known as Serenade QST 713®, Serenade Soil, Serenade Max, Cease) or strain AQ743 (Accession No. NRRL B-21665) or strain AQ 153 (ATCC accession No. 55614) or *B. subtilis* var. *amyloliquefaciens* strain FZB24 (products known as Taegro).

In particular this invention is directed to mixtures comprising the compound (A1), (A2), (A3), (A4), (A5), (A6), (A7), (A8), (A9), (A10), (A11), (A12), (A13), (A14), (A15), (A16) (A17), (A18), (A19) or (A20) as compound of formula (I) and at least one compound selected among:

*Bacillus pumilus*, in particular strain GB34 (products known as Yield Shield®) or strain QST2808 (Accession No. NRRL B-30087, products known as Sonata QST 2808®) or strain AQ717 (Accession No. NRRL B21662), or

*Bacillus subtilis*, in particular strain GB03 (products known as Kodiak®) or strain QST713/AQ713 (Accession No. NRRL B-21661, products known as Serenade QST 713®, Serenade Soil, Serenade Max, Cease) or strain AQ743 (Accession No. NRRL B-21665) or strain AQ 153 (ATCC accession No. 55614) or *B. subtilis* var. *amyloliquefaciens* strain FZB24 (products known as Taegro).

In particular this invention is directed to mixtures comprising the compound (A1), (A2), (A3), (A4), (A5), (A6), (A7), (A8), (A9), (A10), (A11), (A12), (A13), (A14), (A15), (A16) (A17), (A18), (A19) or (A20) as compound of formula (I) and at least strain QST2808 (Accession No. NRRL B-30087, products known as Sonata QST 2808®) or strain QST713/AQ713 (Accession No. NRRL B-21661, products known as Serenade QST 713®, Serenade Soil, Serenade Max, Cease).

If the active compounds in the active compound combinations according to the invention are present in certain weight ratios, the synergistic effect is particularly pronounced. However, the weight ratios of the active compounds in the active compound combinations can be varied within a relatively wide range.

In regard to compound A, the dose of active compound usually applied in the method of treatment according to the invention is generally and advantageously from 10 to 800 g/ha, preferably from 30 to 300 g/ha for applications in foliar treatment. The dose of active substance applied is generally and advantageously from 2 to 200 g per 100 kg of seed, preferably from 3 to 150 g per 100 kg of seed in the case of seed treatment.

In regard to compound B, the dose of active compound usually applied in the method of treatment according to the invention is generally and advantageously from 5 to 10000 g/ha, preferably from 10 to 5000 g/ha for applications in foliar treatment. The dose of active substance applied is generally and advantageously from 2 to 5000 g per 100 kg of seed, preferably from 2 to 2000 g per 100 kg of seed in the case of seed treatment.

it is clearly understood that a person skilled in the art will know how to adapt the application dose, notably according to the nature of said compounds A and B, to the nature of the plant or crop to be treated.

In the method of the invention, active compound combinations according to the invention are applied to leaves in a dose from 0.1 to 10 000 g/ha and are applied to seeds in a dose from 2 to 2000 g per 100 kg of seed.

Where a compound (A) or (B) can be present in tautomeric form, such a compound is understood hereinabove and hereinbelow also to include, where applicable, corresponding tautomeric forms, even when these are not specifically mentioned in each case.

Compounds (A) or (B) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or arylsulfonic acids, e.g. methane- or p-toluene-sulfonic acid. Compounds (A) or (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compounds (A) or (B) in free form and in the form of their salts, hereinabove and herein below any reference to the free compound (A) or (B) or to their salts should be understood as including also the corresponding salts or the free compounds (A) or (B), respectively, where appropriate and expedient. The equivalent also applies to tautomers of compounds (A) or (B) and to their salts.

According to the invention the expression "combination" stands for the various combinations of compounds (A) and compound (B), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days.

Preferably the order of applying the compounds (A) and compound (B) is not essential for working the present invention. Preferably the "combination" of compound (A) and compound (B) is a composition comprising compound (A) and compound (B).

The present invention furthermore relates to compositions for combating/controlling undesirable microorganisms comprising the active compound combinations according to the invention. Preferably, the compositions are fungicidal compositions comprising agriculturally suitable auxiliaries, solvents, carriers, surfactants or extenders.

Furthermore the invention relates to a method of combating undesirable microorganisms, characterized in that the active compound combinations according to the invention are applied to the phytopathogenic fungi and/or their habitat.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as butane, propane, nitrogen and $CO_2$.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 percent by weight, 0.01 and 98 percent by weight, preferable between 0.1 and 95 percent by weight, particularly preferred between 0.5 and 90 percent by weight of the active compound combination according to the invention, very particularly preferable between 10 and 70 percent by weight.

The active compound combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

The compositions according to the invention do not only comprise ready-to-use compositions which can be applied with suitable apparatus to the plant or the seed, but also commercial concentrates which have to be diluted with water prior to use.

The active compound combinations according to the invention can be present in (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and Semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

The invention furthermore comprises a method for treating seed. The invention furthermore relates to seed treated according to one of the methods described in the preceding paragraph.

The active compounds or compositions according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

Accordingly, the present invention also relates in particular to a method for protecting seed and germinating plants against attack by phytopathogenic fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the mixtures according to the invention can be used in particular also for transgenic seed where the plant growing from this seed is capable of expressing a protein which acts against pests. By treating such seed with the active compound combinations or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture or viticulture. In particular, this takes the form of seed of cereals (such as wheat, barley, rye, triticale, millet, oats), maize (corn), cotton, soya bean, rice, potatoes, sunflowers, beans, coffee, beets (e.g. sugar beets and fodder beets), peanuts, oilseed rape, poppies, olives, coconuts, cacao, sugar cane, tobacco, vegetables (such as tomatoes, cucumbers, onions and lettuce), lawn and ornamental plants (also see below). The treatment of seeds of cereals (such as wheat, barley, rye, triticale, and oats), maize (corn) and rice is of particular importance.

As also described further below, the treatment of transgenic seed with the active compound combinations or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularity preferably, the heterologous gene originates from *Bacillus thuringiensis*.

In the context of the present invention, the active compound combinations or compositions according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

Suitable wetting agents that may be present in the seed dressing formulations which can be used according to the invention include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations which can be used according to the invention include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schadlingsbekampfungsmiftel" [Chemistry of Crop Protection Agents and Pesticides], Vol. 2, Springer Verlag, 1970, pp. 401-412).

The seed dressing formulations which can be used according to the invention may be used directly or after dilution with water beforehand to treat seed of any of a very wide variety of types. The seed dressing formulations which can be used according to the invention or their dilute preparations may also be used to dress seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The active compounds or compositions according to the invention have strong microbicidal activity and can be used for controlling unwanted microorganisms, such as fungi and bacteria, in crop protection and material protection.

In crop protection, fungicides can be used for controlling *Plasmodiophoromycetes, Oomycetes, Chytridiomycetes, Zygomycetes, Ascomycetes, Basidiomycetes* and *Deuteromycetes*.

In crop protection, bactericides can be used for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compound combinations or compositions according to the invention, which are applied to the seed, the plant or plant parts, the fruit or the soil in which the plants grow. Preference is given to application onto the plant or the plant parts, the fruits or the soil in which the plants grow.

The compositions according to the invention for combating phytopathogenic fungi in crop protection comprise an active, but non-phytotoxic amount of the compounds according to the invention. "Active, but non-phytotoxic amount" shall mean an amount of the composition according to the invention which is sufficient to control or to completely kill the plant disease caused by fungi, which amount at the same time does not exhibit noteworthy symptoms of phytotoxicity. These application rates generally may be varied in a broader range, which rate depends on several factors, e.g. the phytopathogenic fungi, the plant or crop, the climatic conditions and the ingredients of the composition according to the invention.

The fact that the active compounds, at the concentrations required for the controlling of plant diseases, are well tolerated by plants permits the treatment of aerial plant parts, of vegetative propagation material and seed, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, tubers, corms and rhizomes are listed. Crops and vegetative and generative propagating material, for example cuttings, corms, rhizomes, tubers, runners and seeds also belong to plant parts.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material. They may be preferably employed as crop protection agents. They are active against normally sensitive and resistant species and against all or some stages of development.

Among the plants that can be protected by the method according to the invention, mention may be made of major field crops like corn, soybean, cotton, *Brassica* oilseeds such as *Brassica* napes (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucur-* bitaceae sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak Choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), Malvaceae (for instance okra), *Asparagaceae* (for instance asparagus); horticultural and forest crops; ornamental plants; as well as genetically modified homologues of these crops.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 28 days, preferably 1 to 14 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a *Petunia* EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes. Plants expressing EPSPS genes that confer glyphosate tolerance are described. Plants comprising other genes that confer glyphosate tolerance, such as decarboxylase genes, are described.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPDtolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712). The production of sulfonylurea-tolerant plants and imidazolinone-tolerant plants is described. Other imidazolinone-tolerant plants are also described. Further sulfonylurea- and imidazolinone-tolerant plants are also described.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof; such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1 A or Cry1F proteins and the Cry2Aa or Cry2Ab or Cry2Ae proteins (U.S. patent application Ser. No. 12/214, 022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. Nos. 61/126,083 and 61/195,019), or the binary toxin made up of the VIP3 protein and the Cry2Aa or Cry2Ab or Cry2Ae proteins (U.S. patent application Ser. No. 12/214, 022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants.

2) plants which contain a stress tolerance enhancing transgene capable of reducing the expression and/or the activity of the PARG encoding genes of the plants or plants cells.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha-1,4-glucans, plants producing alpha-1,6 branched alpha-1,4-glucans, plants producing alternan, 3) transgenic plants which produce hyaluronan, 4) transgenic plants or hybrid plants, such as onions with characteristics such as 'high soluble solids content', 'low pungency' (LP) and/or 'long storage' (LS).

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes;
b) Plants, such as cotton plants, containing an altered form of rsw2 or rsw3 homologous nucleic acids Plants, such as cotton plants, with increased expression of sucrose phosphate synthase;
c) Plants, such as cotton plants, with increased expression of sucrose synthase;
d) Plants, such as cotton plants, wherein the timing of the plasmodesmatal gating at the basis of the fiber cell is altered, e.g. through downregulation of fiber-selective β-1,3-glucanase;
e) Plants, such as cotton plants, having fibers with altered reactivity, e.g. through the expression of N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content.
b) Plants such as oilseed rape plants, producing oil having a low linolenic acid content.
c) Plant such as oilseed rape plants, producing oil having a low level of saturated fatty acids.

Plants or plant cultivars (that can be obtained by plant biotechnology methods such as genetic engineering) which may also be treated according to the invention are plants, such as potatoes which are virus-resistant, e.g. against potato virus Y (event SY230 and SY233 from Tecnoplant, Argentina), which are disease resistant, e.g. against potato late blight (e.g. RB gene), which show a reduction in cold-induced sweetening (carrying the Nt-Inhh, IIR-INV gene) or which possess a dwarf phenotype (Gene A-20 oxidase).

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for non-regulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Particularly useful transgenic plants which may be treated according to the invention are plants which comprise one or more genes which encode one or more toxins, such as the following which are sold under the trade names YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B®(cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMF® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Additional particularly useful plants containing single transformation events or combinations of transformation events are listed for example in the databases from various national or regional regulatory agencies (see for example http://gmoinfo.jrc.it/gmp_browse.aspx and http://ceragm-c.org/index.php?evidcode=&hstIDXCode=&gType=& AbbrCode=&atCode=&stCode=&coID Code=&action=gm_crop_database&mode=Submit).

In material protection the substances of the invention may be used for the protection of technical materials against infestation and destruction by undesirable fungi and/or microorganisms.

Technical materials are understood to be in the present context non-living materials that have been prepared for use in engineering. For example, technical materials that are to be protected against micro-biological change or destruction by the active materials of the invention can be adhesives, glues, paper and cardboard, textiles, carpets, leather, wood, paint and plastic articles, cooling lubricants and other materials that can be infested or destroyed by micro-organisms. Within the context of materials to be protected are also parts of production plants and buildings, for example cooling circuits, cooling and heating systems, air conditioning and ventilation systems, which can be adversely affected by the propagation of fungi and/or microorganisms. Within the context of the present invention, preferably mentioned as technical materials are adhesives, glues, paper and cardboard, leather, wood, paints, cooling lubricants and heat exchanger liquids, particularly preferred is wood. The combinations according to the invention can prevent disadvantageous effects like decaying, dis- and decoloring, or molding. The active compound combinations and compositions according to the invention can likewise be employed for protecting against colonization of objects, in particular ship hulls, sieves, nets, buildings, quays and signalling installations, which are in contact with sea water or brackish water.

The method of treatment according to the invention can also be used in the field of protecting storage goods against attack of fungi and microorganisms. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood.

Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

Diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladosporium* species, such as, for example, *Cladosporium cucumerinum*; *Cochliobolus* species, such as, for example, *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans* and *Leptosphaeria nodorum*; *Magnaporthe* species, such as, for example, *Magnaporthe grisea*; *Microdochium* species, such as, for example, *Microdochium nivale*; *Mycosphaerella* species, such as, for example, *Mycosphaerella graminicola*, *Mycosphaerella arachidicola* and *Mycosphaerella fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium secalis*; *Septoria* species, such as, for example, *Septoria apii* and *Septoria lycopersici*; *Typhula* species, such as, for example, *Typhula incarnata*; *Venturia* species, such as, for example, *Venturia inaequalis*;

Root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Rhizoctonia* species, such as, for example *Rhizoctonia solani*; *Tapesia* species, such as, for example, *Tapesia acuformis*; *Thielaviopsis* species, such as, for example, *Thielaviopsis basicola*;

Ear and panicle diseases (including maize cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Septoria* species, such as for example, *Septoria nodorum*; Seed- and soil-borne decay, mould, wilt, rot and damping-off diseases, caused, for example, by *Alternaria* diseases caused for example by *Alternaria brassicicola*; *Aphanomyces* diseases caused for example by *Aphanomyces euteiches*; *Ascochyta* diseases caused for example by *Ascochyta lentis*; *Aspergillus* diseases caused for example by *Aspergillus flavus*; *Cladosporium* diseases caused for example by *Cladosporium herbarum*; *Cochliobolus* diseases caused for example by *Cochliobolus sativus*; (Conidiaform: *Drechslera*, *Bipolaris* Syn: *Helminthosporium*); *Colletotrichum* diseases caused for example by *Colletotrichum coccodes*; *Fusarium* diseases caused for example by *Fusarium culmorum*; *Gibberella* diseases caused for example by *Gibberella zeae*; *Macrophomina* diseases caused for example by *Macrophomina phaseolina*; *Microdochium* diseases caused for example by *Microdochium nivale*; *Monographella* diseases caused for example by *Monographella nivalis*; *Penicillium* diseases caused for example by *Penicillium expansum*; *Phoma* diseases caused for example by *Phoma lingam*; *Phomopsis* diseases caused for example by *Phomopsis sojae*; *Phytophthora* diseases caused for example by *Phytophthora cactorum*; *Pyrenophora* diseases caused for example by *Pyrenophora graminea*; *Pyricularia* diseases caused for example by *Pyricularia oryzae*; *Pythium* diseases caused for example by *Pythium ultimum*; *Rhizoctonia* diseases caused for example by *Rhizoctonia solani*; *Rhizopus* diseases caused for example by *Rhizopus oryzae*; *Sclerotium* diseases caused for example by *Sclerotium rolfsii*; *Septoria* diseases caused for example by *Septoria nodorum*; *Typhula* diseases caused for example by *Typhula incarnata*; *Verticillium* diseases caused for example by *Verticillium dahliae*;

Diseases caused by smut and bunt fungi, such as, for example, *Sphacelotheca* species, such as, for example, *Sphacelotheca reiliana*; *Tilletia* species, such as, for example, *Tilletia caries*; *T. controversa*; *Urocystis* species, such as, for example, *Urocystis occulta*; *Ustilago* species, such as, for example, *Ustilago nuda*; *U. nuda tritici*;

Fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotiorum*; *Verticilium* species, such as, for example, *Verticilium alboatrum*;

Seed- and soil-borne rot and wilt diseases, and also diseases of seedlings, caused, for example, by *Fusarium* species, such as, for example, *Fusarium culmorum*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*;

Deformations of leaves, flowers and fruits caused, for example, by *Taphrina* species, such as, for example, *Taphrina deformans*;

Degenerative diseases of woody plants caused, for example, by *Esca* species, such as, for example, *Phaemoniella clamydospora* and *Phaeoacremonium aleophilum* and *Fomitiporia mediterranea*;

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani*; *Helminthosporium* species, such as, for example, *Helminthosporium solani*;

Diseases caused by bacteriopathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soya beans:

Fungal diseases on leaves, stems, pods and seeds caused, for example, by *alternaria* leaf spot (*Alternaria* spec. atrans tenuissima), anthracnose (*Colletotrichum gloeosporoides dematium* var. truncatum), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. cauliivora), phytophthora rot (*Phytophthora megasperma*), brown stem rot (*Phialophora gregata*), pythium rot (*Pythium aphanidermatum, Pythium iffegulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

It is also possible to control resistant strains of the organisms mentioned above.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae. Microorganisms of the following genera may be mentioned as examples: *Alternaria*, such as *Alternaria tenuis*, *Aspergillus*, such as *Aspergillus niger*, *Chaetomium*, such as *Chaetomium globosum*, *Coniophora*, such as *Coniophora puetana*, *Lentinus*, such as *Lentinus tigrinus*, *Penicillium*, such as *Penicillium glaucum*, *Polyporus*, such as *Polyporus versicolor*, *Aureobasidium*, such as *Aureobasidium pullulans*, *Sclerophoma*, such as *Sclerophoma pityophila*, *Trichoderma*, such as *Trichoderma viride*, *Escherichia*, such as *Escherichia coli*, *Pseudomonas*, such as *Pseudomonas aeruginosa*, and *Staphylococcus*, such as *Staphylococcus aureus*.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum*, *Aspergillus* species such as *Aspergillus niger* and *Aspergillus fumigatus*, *Trichophyton* species such as *Trichophyton mentagrophytes*, *Microsporon* species such as *Microsporon canis* and *audouinii*. The list of these fungi by no means limits the mycotic spectrum which can be covered, but is only for illustration.

When applying the compounds according to the invention the application rates can be varied within a broad range. The dose of active compound/application rate usually applied in the method of treatment according to the invention is generally and advantageously for treatment of part of plants, e.g. leafs (foliar treatment): from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 1 to 200 g per 100 kg of seed, preferably from 2 to 150 g per 100 kg of seed, more preferably from 2.5 to 25 g per 100 kg of seed, even more preferably from 2.5 to 25 g per 100 kg of seed;
for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The combination according to the invention can be used in order to protect plants within a certain time range after the treatment against pests and/or phytopathogenic fungi and/or microorganisms. The time range, in which protection is effected, spans in general 1 to 28 days, preferably 1 to 14 days, more preferably 1 to 10 days, even more preferably 1 to 7 days after the treatment of the plants with the combinations or up to 200 days after the treatment of plant propagation material.

Furthermore combinations and compositions according to the invention may also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2-und HT2-Toxins, Fumonisines, Zearalenone Moniliformine, Fusarine, Diaceotxyscirpenole (DAS), Beauvericine, Enniatine, Fusaroproliferine, Fusarenole, Ochratoxines, Patuline, Ergotalkaloides und Aflatoxines, which are caused for example by the following fungal diseases: *Fusarium* spec., like *Fusarium acuminatum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

The compounds of the formula (I) or salts thereof in combination with compounds (B), (C) or (D) are also suitable for the selective control of harmful organisms in a number of plant crops, for example in crops of economic importance, such as cereals (wheat, barley, triticale, rye, rice, corn, millet), sugar beet, sugar cane, oilseed rape, cotton, sunflower, peas, beans and soybeans. Of particular interest is the use in monocotyledonous crops, such as cereals (wheat, barley, rye, triticale, sorghum), including corn and rice, and monocotyledonous vegetable crops, but also in dicotyledonous crops, such as, for example, soybean, oilseed rape, cotton, grape vines, vegetable plants, fruit plants and ornamental plants. The combinations are preferred for the selective control of harmful plants in useful plants (crops). The combinations according to the invention are also suitable for controlling harmful plants in beds and plots of useful plants and ornamental plants, such as, for example, lawn plots with useful or ornamental lawn, especially lolium, meadow grass or Bermuda grass.

Also of interest from among the useful plants or crop plants in which the combinations according to the invention may be used are mutant crops which are completely or partially tolerant to certain pesticides or completely or partially tolerant transgenic crops, for example corn crops which are resistant to glufosinate or glyphosate, or soybean crops which are resistant to herbicidal imidazolinones. However, the particular advantage of the combinations in this novel way is their efficient action in crops which normally are insufficiently tolerant to the pesticides being applied.

Accordingly, the invention also provides a method for the selective control of harmful plants in crops of useful plants which comprises applying an effective useful-plant-protecting amount of one or more compounds (I) in combination with compounds (B) or salts thereof before, after or simultaneously with an amount, effective against harmful plants, of one or more herbicides to the plants, parts of plants, plant seeds or seed.

N-cyclopropyl amides of formula (I) wherein T represents an oxygen atom, can be prepared by condensation of a substituted N-cyclopropyl benzylamine with 3-(difluoromethyl)-5-fluoro-1-methyl-1H-pyrazole-4-carbonyl chloride according to WO-2007/087906 (process P1) and WO-2010/130767 (process P1—step 10).

Substituted N-cyclopropyl benzylamines are known or can be prepared by known processes such as the reductive amination of a substituted aldehyde with cyclopropanamine (*J. Med. Chem.*, 2012, 55 (1), 169-196) or by nucleophilic substitution of a substituted benzyl alkyl (or aryl)sulfonate or a substituted benzyl halide with cyclopropanamine (*Bioorg. Med. Chem.*, 2006, 14, 8506-8518 and WO2009/140769).

3-(difluoromethyl)-5-fluoro-1-methyl-1H-pyrazole-4-carbonyl chloride can be prepared according to WO-2010/130767 (process P1—steps 9 or 11)

N-cyclopropyl thioamides of formula (I) wherein T represents a sulfur atom, can be prepared by thionation of a N-cyclopropyl amide of formula (I) wherein T represents a oxygen atom, according to WO-2009/016220 (process P1) and WO-2010/130767 (process P3).

The following examples illustrate in a non limiting manner the preparation of the compounds of formula (I) according to the invention.

Preparation of N-cyclopropyl-3-(difluoromethyl)-5-fluoro-N-(2-isopropylbenzyl)-1-methyl-1H-pyrazole-4-carboxamide (compound A1)

Step A: preparation of N-(2-isopropylbenzyl)cyclopropanamine

To a solution of 55.5 g (971 mmol) of cyclopropanamine in 900 mL of methanol, are successively added 20 g of 3 Å molecular sieves and 73 g (1.21 mol) of acetic acid. 72 g (486 mmol) of 2-isopropyl-benzaldehyde are then added dropwise and the reaction mixture is further heated at reflux for 4 hours.

The reaction mixture is then cooled to 0° C. and 45.8 g (729 mmol) of sodium cyanoborohydride are added by portion in 10 min and the reaction mixture is stirred again for 3 hours at reflux. The cooled reaction mixture is filtered over a cake of diatomaceous earth. The cake is washed abundantly by methanol and the methanolic extracts are concentrated under vacuum. Water is then added to the residue and the pH is adjusted to 12 with 400 mL of a 1 N aqueous solution of sodium hydroxide. The watery layer is extracted with ethyl acetate, washed by water (2×300 mL) and dried over magnesium sulfate to yield 81.6 g (88%) of N-(2-isopropylbenzyl)cyclopropanamine as a yellow oil used as such in the next step.

The hydrochloride salt can be prepared by dissolving N-(2-isopropylbenzyl)cyclopropanamine in diethyl-ether (1.4 mL/g) at 0° C. followed by addition of a 2 M solution of hydrochloric acid in diethylether (1.05 eq.). After a 2 hours stirring, N-(2-isopropylbenzyl)cyclopropanamine hydrochloride (1:1) is filtered off, washed by diethylether and dried under vacuum at 40° C. for 48 hours. Mp (melting point)=149° C.

Step B: preparation of N-cyclopropyl-3-(difluoromethyl)-5-fluoro-N-(2-isopropylbenzyl)-1-methyl-1H-pyrazole-4-carboxamide To 40.8 g (192 mmol) of N-(2-isopropylbenzyl)cyclopropanamine in 1 L of dry tetrahydrofurane are added at room temperature, 51 mL (366 mmol) of triethylamine. A solution of 39.4 g (174 mmol) of 3-(difluoromethyl)-5-fluoro-1-methyl-1H-pyrazole-4-carbonyl chloride in 800 mL of dry tetrahydrofurane is then added dropwise while maintaining the temperature below 34° C. The reaction mixture is heated at reflux for 2 hours then left overnight at room temperature. Salts are filtered off and the filtrate is concentrated under vacuum to yield 78.7 g of a brown oil. Column chromatography on silica gel (750 g—gradient n-heptane/ethyl acetate) yields 53 g (71% yield) of N-cyclopropyl-3-(difluoromethyl)-5-fluoro-N-(2-isopropylbenzyl)-1-methyl-1H-pyrazole-4-carboxamide as a yellow oil that slowly crystallizes. Mp=76-79° C.

In the same way, compounds A2 to A19 can be prepared according to the preparation described for compound A1.

Preparation of N-cyclopropyl-3-(difluoromethyl)-5-fluoro-N-(2-isopropylbenzyl)-1-methyl-1H-pyrazole-4-carbothioamide (compound A20)

A solution of 14.6 g (65 mmol) of phosphorus pentasulfide and 48 g (131 mmol) of N-cyclopropyl-3-(difluoromethyl)-5-fluoro-N-(2-isopropylbenzyl)-1-methyl-1H-pyrazole-4-carboxamide in 500 ml of dioxane are heated at 100° C. for 2 hours. 50 ml of water are then added and the reaction mixture is further heated at 100° C. for another hour. The cooled reaction mixture is filtered over a basic alumina cartridge. The cartridge is washed by dichloromethane and the combined organic extracts are dried over magnesium sulfate and concentrated under vacuum to yield 55.3 g of an orange oil. The residue is tritured with a few mL of diethylether until crystallisation occurs. Crystals are filtered off and dried under vacuum at 40° C. for 15 hours to yield 46.8 g (88% yield) of N-cyclopropyl-3-(difluoromethyl)-5-fluoro-N-(2-isopropylbenzyl)-1-methyl-1H-pyrazole-4-carbothioamide. Mp=64-70° C.

Table 1 provides the log P and NMR data ($^1$H) of compounds A1 to A20.

In table 1, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

| Cmpd | logP | NMR |
|---|---|---|
| A1 | 3.35 | $^1$H NMR (500 MHz, CHCl$_3$-d): δ ppm 0.64 (bs, 4H), 1.21 (d, J = 6.60 Hz, 6H), 2.44-2.80 (m, 1H), 3.01-3.29 (m, 1H), 3.78 (s, 3H), 4.76 (bs, 2H), 6.89 (t, J = 54.70 Hz, 1H), 7.12-7.33 (m, 4H). |
| A2 | 3.44 | $^1$H NMR (500 MHz, CHCl$_3$-d): δ ppm 0.47-0.77 (m, 6H), 0.80-1.04 (m, 2H), 1.92 (bs, 1H), 2.66 (bs, 1H), 3.80 (s, 3H), 4.92 (bs, 2H), 6.90 (t, J = 54.50 Hz, 1H), 7.01-7.25 (m, 4H). |
| A3 | 4.06 | $^1$H NMR (500 MHz, CHCl$_3$-d): δ ppm 0.61 (bs, 4H), 1.46 (s, 9H), 2.77-2.98 (m, 1H), 3.89 (s, 3H), 5.05 (bs, 2H), 6.91 (t, J = 54.70 Hz, 1H), 7.20 (bs, 3H), 7.35-7.48 (m, 1H). |
| A4 | 3.76 | $^1$H NMR (300 MHz, CHCl$_3$-d): δ ppm 0.65-0.69 (m, 4H), 1.21 (t, 3H), 2.62-2.64 (m, 3H), 3.81 (s, 3H), 4.70 (s, 2H), 6.85 (t, J = 54.6 Hz, 1H), 7.04-7.22 (m, 3H). |
| A5 | 4.09 | $^1$H NMR (500 MHz, CHCl$_3$-d): δ ppm 0.63-0.73 (m, 4H), 1.22 (d, J = 6.92Hz, 6H), 2.59-2.87 (m, 1H), 2.98-3.30 (m, 1H), 3.82 (s, 3H), 4.74 (bs, 2H), 6.88 (t, J = 54.40 Hz, 1H), 7.20-7.27 (m, 3H). |
| A6 | 3.41 | $^1$H NMR (300 MHz, CHCl$_3$-d): δ ppm 0.65-0.66 (m, 4H), 1.21 (t, 3H), 2.62 (q, 2H), 2.64 (bs, 1H), 3.81 (s, 3H), 4.71 (s, 2H), 6.86 (t, J = 54.6 Hz, 1H), 6.89-6.95 (m, 2H), 7.13-7.18 (m, 1H). |
| A7 | 3.70 | $^1$H NMR (300 MHz, CHCl$_3$-d): δ ppm 0.65-0.69 (m, 4H), 1.22 (d, 6H), 2.69 (bs, 1H), 3.10-3.14 (m, 1H), 3.81 (s, 3H), 4.75 (s, 2H), 6.86 (t, J = 54.6 Hz, 1H), 6.88-6.93 (m, 2H), 7.23-7.28 (m, 1H). |
| A8 | 3.46 | $^1$H NMR (300 MHz, CHCl$_3$-d): δ ppm 0.60-0.66 (m, 6H), 0.89-0.95 (m, 2H), 1.82-1.84 (m, 1H), 2.73 (bs, 1H), 3.81 (s, 3H), 4.89 (s, 2H), 6.68-6.99 (m, 4H). |
| A9 | 4.21 | $^1$H NMR (300 MHz, CHCl$_3$-d): δ ppm 0.64-0.68 (m, 4H), 1.56-1.62 (m, 2H), 1.62-1.70 (m, 2H), 1.76-1.83 (m, 2H), 1.96-2.05 (m, 2H), 2.71 (bs, 1H), 3.13-3.19 (m, 1H), 3.81 (s, 3H), 4.76 (s, 2H), 6.86 (t, J = 54.0 Hz, 1H), 6.87-6.97 (m, 2H), 7.23-7.28 (m, 1H). |
| A10 | 3.65 | $^1$H NMR (400 MHz, CHCl$_3$-d): δ ppm 0.65 (bs, 4H), 1.21 (d, J = 6.75 Hz, 5H), 2.29-2.59 (m, 1H), 3.00-3.36 (m, 1H), 3.79 (s, 3H), 4.83 (s, 2H), 6.68-7.06 (m, 2H), 7.13 (d, J = 7.78 Hz, 1H), 7.27-7.33 (m, 1H). |
| A11 | 3.70 | $^1$H NMR (500 MHz, CHCl$_3$d): δ ppm 0.65 (bs, 4H), 2.31 (s, 3H), 2.64 (m, 1H), 3.81 (s, 3H), 4.73 (bs, 2H), 6.89 (t, J = 54.6 Hz, 1H), 7.01-7.14 (m, 3H). |
| A12 | 3.99 | $^1$H NMR (500 MHz, CHCl$_3$-d): δ ppm 0.66 (bs, 4H), 1.22 (d, J = 6.97 Hz, 6H), 2.31 (s, 3H), 2.54-2.75 (m, 1H), 2.99-3.25 (m, 1H), 3.81 (s, 3H), 4.75 (bs, 2H), 6.89 (t, J = 53.90Hz, 1H), 7.01-7.23 (m, 3H). |
| A13 | 3.76 | $^1$H NMR (500 MHz, CHCl$_3$-d): δ ppm 0.61-0.68 (m, 6H), 0.80-1.00 (m, 2H), 1.74-2.00 (m, 1H), 2.31 (s, 3H), 2.53-2.82 (m, 1H), 3.81 (s, 3H), 4.89 (bs, 2H), 6.83 (t, J = 54.80 Hz, 1H), 6.91-7.06 (m, 3H). |
| A14 | 4.36 | $^1$H NMR (500 MHz, CHCl$_3$-d): δ ppm 0.62 (m, 4H), 1.44 (s, 9H), 2.28 (s, 3H), 2.74-3.02 (m, 1H), 3.83 (bs, 3H), 5.02 (bs, 2H), 6.85 (t, J = 54.40 Hz, 1 H), 7.01 (bs, 1H), 7.21-7.29 (m, 2H). |

-continued

| Cmpd | logP | NMR |
|---|---|---|
| A15 | 3.80 | $^1$H NMR (500 MHz, CHCl$_3$-d): δ ppm 0.50-0.67 (m, 4H), 2.81 (bs, 1H), 3.78 (s, 3H), 4.85 (bs, 2H), 6.78 (t, J = 55.00 Hz, 1H), 7.20-7.29 (m, 2H), 7.54 (d, J = 8.17 Hz, 1H). |
| A16 | 3.78 | $^1$H NMR (500 MHz, CHCl$_3$-d): δ ppm 0.55-0.70 (m, 4H), 2.37 (s, 3H), 2.72-3.04 (m, 1H), 3.83 (bs, 3H), 4.91 (bs, 2H), 6.86 (t, J = 54.50 Hz, 1H), 7.10-7.20 (m, 2H), 7.54 (d, J = 7.89 Hz, 1H). |
| A17 | 3.46 | $^1$H NMR (500 MHz, CHCl$_3$-d): δ ppm 0.47-0.64 (m, 4H), 2.29-2.55 (m, 1H), 3.80 (s, 3H), 5.05 (s, 2H), 6.95 (t, J = 54.40 Hz, 1H), 7.40 (t, J = 7.86 Hz, 1H), 7.60-7.70 (dd, 2H). |
| A18 | 3.62 | $^1$H NMR (500 MHz, CHCl$_3$-d): δ ppm 0.50-0.74 (m, 4H), 2.45-2.71 (m, 1H), 3.81 (s, 3H), 4.99 (s, 2H), 6.91 (t, J = 54.40 Hz, 1H), 7.45-7.57 (m, 2H). |
| A19 | 4.04 | $^1$H NMR (500 MHz, CHCl$_3$-d): δ ppm 0.65 (bs, 4H), 1.20 (t, J = 7.43 Hz, 3H), 2.22 (s, 3H), 2.24 (s, 3H), 2.58-2.64 (m, 2H), 3.80 (s, 3H), 4.70 (bs, 2H), 6.89 (t, J = 54.70 Hz, 3H), 6.98 (bs, 2H). |
| A20 | 4.36 | $^1$H NMR (500 MHz, CHCl$_3$-d): δ ppm 0.55-0.84 (m, 4H), 1.27 (d, J = 6.97 Hz, 6H), 2.73-2.85 (m, 1H), 3.04-3.23 (m, 1H), 3.80 (s, 3H), 4.60-5.06 (m, 1H), 6.99-7.38 (m, 5H). |

The advanced fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually. The expected activity for a given combination of two active compounds can be calculated as follows (cf. Colby, S. R., "Calculating Synergistic and Antagonistic Responses of Herbicide Combinations", *Weeds* 1967, 15, 20-22):

If

X is the efficacy when active compound A is applied at an application rate of m ppm (or g/ha), Y is the efficacy when active compound B is applied at an application rate of n ppm (or g/ha), E is the efficacy when the active compounds A and B are applied at application rates of m and n ppm (or g/ha), respectively, and then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in *Neth. J. Plant Path.*, 1964, 70, 73-80).

The invention is illustrated by the following examples. However the invention is not limited to the examples.

Used compounds of biological control agents are the commercially available products SERENADE-MAX® and SONATA®. The application rate of SERENADE-MAX® (1.48) refers to the amount of dried *Bacillus subtilis* strain QST713 (Accession No. NRRL B-21661), contained in the ready for use product. The application rate of SONATA® (1.44) refers to the amount of dried *Bacillus pumilus* strain QST2808 (Accession No. NRRL B-30087), contained in the ready for use product.

EXAMPLE A

*Puccinia triticina*-Test (Wheat)/Preventive

The commercially available compounds SERENADE-MAX®, SONATA®, active compounds (1 part by weight) solved in N,N-dimethylacetamide (49 parts by weight) and alkylaryl polyglycol ether (1 part by weight), or combinations thereof were diluted with water to the desired concentration.

To test for preventive activity, young plants are sprayed with the preparation of active compound or active compound combination at the stated rate of application.

After the spray coating has been dried, the plants are sprayed with a spore suspension of *Puccinia triticina*. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

The table below clearly shows that the observed activity of the active compound combination according to the invention is greater than the calculated activity, i.e. a synergistic effect is present.

TABLE A

*Puccinia triticina*-test (wheat)/preventive

| Active compounds | Application rate of active compound in ppm a.i. | Efficacy in % found* | calc.** |
|---|---|---|---|
| (A5) N-(5-chloro-2-isopropylbenzyl)-N-cyclopropyl-3-(difluoromethyl)-5-fluoro-1-methyl-1H-pyrazole-4-carboxamide | 30 | 67 | |

TABLE A-continued

Puccinia triticina-test (wheat)/preventive

| Active compounds | Application rate of active compound in ppm a.i. | Efficacy in % found* | calc.** |
|---|---|---|---|
| (1.48) SERENADE-MAX ® | 5000 | 22 | |
| (1.44) SONATA ® | 5000 | 33 | |
| (A5) + (1.48) 1:167 | 30 + 5000 | 100 | 74 |
| (A5) + (1.44) 1:167 | 30 + 5000 | 89 | 78 |

*found = activity found
**calc. = activity calculated using Colby's formula

EXAMPLE B

Pyrenophora teres-Test (Barley)/Preventive

The commercially available compounds SERENADE-MAX®, SONATA®, active compounds (1 part by weight) solved in N,N-dimethylacetamide (49 parts by weight) and alkylaryl polyglycol ether (1 part by weight), or combinations thereof were diluted with water to the desired concentration.

To test for preventive activity, young plants are sprayed with the preparation of active compound or active compound combination at the stated rate of application.

After the spray coating has been dried, the plants are sprayed with a spore suspension of Pyrenophora teres. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

The table below clearly shows that the observed activity of the active compound combination according to the invention is greater than the calculated activity, i.e. a synergistic effect is present.

TABLE B

Pyrenophora teres-test (barley)/preventive

| Active compounds | Application rate of active compound in ppm a.i. | Efficacy in % found* | calc.** |
|---|---|---|---|
| (A5) N-(5-chloro-2-isopropylbenzyl)-N-cyclopropyl-3-(difluoromethyl)-5-fluoro-1-methyl-1H-pyrazole-4-carboxamide | 30 | 78 | |
| (1.48) SERENADE-MAX ® | 5000 | 33 | |
| (1.44) SONATA ® | 5000 | 67 | |
| (A5) + (1.48) 1:167 | 30 + 5000 | 100 | 85 |
| (A5) + (1.44) 1:167 | 30 + 5000 | 100 | 93 |

*found = activity found
**calc. = activity calculated using Colby's formula

EXAMPLE C

Septoria tritici-Test (Wheat)/Preventive

The commercially available compounds SERENADE-MAX®, SONATA®, active compounds (1 part by weight) solved in N,N-dimethylacetamide (49 parts by weight) and alkylaryl polyglycol ether (1 part by weight), or combinations thereof were diluted with water to the desired concentration.

To test for preventive activity, young plants are sprayed with the preparation of active compound or active compound combination at the stated rate of application.

After the spray coating has been dried, the plants are sprayed with a spore suspension of Septoria tritici. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed.

The table below clearly shows that the observed activity of the active compound combination according to the invention is greater than the calculated activity, i.e. a synergistic effect is present.

TABLE C

Septoria tritici-test (wheat)/preventive

| Active compounds | Application rate of active compound in ppm a.i. | Efficacy in % found* | calc.** |
|---|---|---|---|
| (A5) N-(5-chloro-2-isopropylbenzyl)-N-cyclopropyl-3-(difluoromethyl)-5-fluoro-1-methyl-1H-pyrazole-4-carboxamide | 30 | 60 | |
| (1.48) SERENADE-MAX ® | 5000 | 20 | |
| (1.44) SONATA ® | 5000 | 20 | |
| (A5) + (1.48) 1:167 | 30 + 5000 | 100 | 68 |
| (A5) + (1.44) 1:167 | 30 + 5000 | 100 | 68 |

*found = activity found
**calc. = activity calculated using Colby's formula

The invention claimed is:
1. An active compound combination comprising
(A) at least one derivative of formula (I)

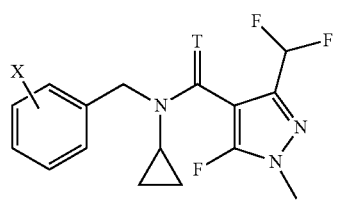

(I)

wherein T represents an oxygen atom and X is selected from the group consisting of 2-isopropyl, 2-cyclopropyl, 2-tert-butyl, 5-chloro-2-ethyl, 5-chloro-2-isopropyl, 2-ethyl-5- fluoro, 5-fluoro-2-isopropyl, 2-cyclopropyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl) and 2-ethyl-4,5-dimethyl, or an agrochemically acceptable salt thereof,
and
  (B) at least one biological control agent selected from the group consisting of *Bacillus pumilis* and *Bacillus subtilis*, wherein the combination of (A) and (B) exhibits synergy.

2. The active compound combination according to claim 1, wherein the compound of the formula (I) is selected from the group consisting of:
  N-cyclopropyl-3-(difluoromethyl)-5-fluoro-N-(2-isopropylbenzyl)-1-methyl-1H-pyrazole-4-carboxamide (compound A1),
  N-cyclopropyl-N-(2-cyclopropylbenzyl)-3-(difluoromethyl)-5-fluoro-1-methyl-1H-pyrazole-4-carboxamide (compound A2),
  N-(2-tert-butylbenzyl)-N-cyclopropyl-3-(difluoromethyl)-5-fluoro-1-methyl-1H-pyrazole-4-carboxamide (compound A3),
  N-(5-chloro-2-ethylbenzyl)-N-cyclopropyl-3-(difluoromethyl)-5-fluoro-1-methyl-1H-pyrazole-4-carboxamide (compound A4),
  N-(5-chloro-2-isopropylbenzyl)-N-cyclopropyl-3-(difluoromethyl)-5-fluoro-1-methyl-1H-pyrazole-4-carboxamide (compound A5),
  N-cyclopropyl-3-(difluoromethyl)-N-(2-ethyl-5-fluorobenzyl)-5-fluoro-1-methyl-1H-pyrazole-4-carboxamide (compound A6),
  N-cyclopropyl-3-(difluoromethyl)-5-fluoro-N-(5-fluoro-2-isopropylbenzyl)-1-methyl-1H-pyrazole-4-carboxamide (compound A7),
  N-cyclopropyl-N-(2-cyclopropyl-5-fluorobenzyl)-3-(difluoromethyl)-5-fluoro-1-methyl-1H-pyrazole-4-carboxamide (compound A8),
  N-cyclopropyl-3-(difluoromethyl)-5-fluoro-N-(2-fluoro-6-isopropylbenzyl)-1-methyl-1H-pyrazole-4-carboxamide (compound A10),
  N-cyclopropyl-3-(difluoromethyl)-N-(2-ethyl-5-methylbenzyl)-5-fluoro-1-methyl-1H-pyrazole-4-carboxamide (compound A11),
  N-cyclopropyl-3-(difluoromethyl)-5-fluoro-N-(2-isopropyl-5-methylbenzyl)-1-methyl-1H-pyrazole-4-carboxamide (compound A12),
  N-cyclopropyl-N-(2-cyclopropyl-5-methylbenzyl)-3-(difluoromethyl)-5-fluoro-1-methyl-1H-pyrazole-4-carboxamide (compound A13),
  N-(2-tert-butyl-5-methylbenzyl)-N-cyclopropyl-3-(difluoromethyl)-5-fluoro-1-methyl-1H-pyrazole-4-carboxamide (compound A14),
  N-[5-chloro-2-(trifluoromethyl)benzyl]-N-cyclopropyl-3-(difluoromethyl)-5-fluoro-1-methyl-1H-pyrazole-4-carboxamide (compound A15),
  N-cyclopropyl-3-(difluoromethyl)-5-fluoro-1-methyl-N-[5-methyl-2-(trifluoromethyl)benzyl]-1H-pyrazole-4-carboxamide (compound A16),
  N-[2-chloro-6-(trifluoromethyl)benzyl]-N-cyclopropyl-3-(difluoromethyl)-5-fluoro-1-methyl-1H-pyrazole-4-carboxamide (compound A17),
  N-[3-chloro-2-fluoro-6-(trifluoromethyl)benzyl]-N-cyclopropyl-3-(difluoromethyl)-5-fluoro-1-methyl-1H-pyrazole-4-carboxamide (compound A18) and
  N-cyclopropyl-3-(difluoromethyl)-N-(2-ethyl-4,5-dimethylbenzyl)-5-fluoro-1-methyl-1H-pyrazole-4-carboxamide (compound A19).

3. The active compound combination according to claim 2 wherein the compound of the formula (I) is N-(5-chloro-2-isopropylbenzyl)-N-cyclopropyl-3-(difluoromethyl)-5-fluoro-1-methyl-1H-pyrazole-4-carboxamide.

4. The active compound combination according to claim 1 wherein the biological agent is chosen among strain GB34, strain QST2808, strain AQ717, strain GB03, strain QST713/AQ713, strain AQ743, strain AQ 153 or strain FZB24.

5. The active compound combination according to claim 4 wherein the biological agent is chosen among strain QST2808 or strain QST713/AQ713.

6. A composition comprising the active compound combination according to claim 1, and further comprising an auxiliary, solvent, carrier, surfactant or extender.

7. A method for controlling phytopathogenic fungi in crop protection, comprising applying the active compound combination according to claim 1 to the seed, the plant, to fruits of plants or to the soil on which the plant grows or is supposed to grow.

8. The method according to claim 7, comprising treating the plant, the fruits of plants or the soil on which the plant grows or is intended to grow.

9. The method according to claim 7, comprising treating leaves with from 0.1 to 10 000 g/ha or seed with from 2 to 200 g per 100 kg of seed.

10. A method for controlling unwanted phytopathogenic fungi in crops comprising contacting the active compound combination according to claim 1 with said crops for controlling unwanted phytopathogenic fungi in crop protection.

11. A method for treating seed, seed of transgenic plants or transgenic plants comprising contacting the active compound combination according to claim 1 with said seed, seed of transgenic plants or transgenic plants.

12. Seed treated with the active compound combination according to claim 1.

13. A method for the selective control of harmful plants in crops of useful plants, which comprises applying an effective plant-protecting amount of the active compound combination according to claim 1, where the compounds of formula (I) are applied before, after or simultaneously with an effective amount of said biological control agent to the plants, parts of plants, plant seeds or the seed.

14. The method according to claim 13, which comprises treating the seed with one or more compounds of the formula (I) or salts thereof and applying one or more of said biological control agents after sowing by the pre-emergence method or by the post-emergence method.

15. A method for controlling phytopathogenic fungi in crop protection, comprising applying the composition according to claim 6 to the seed, the plant, to fruits of plants or to the soil on which the plant grows or is supposed to grow.

16. A method for controlling unwanted phytopathogenic fungi in crop protection comprising contacting the composition of claim 6 with said phytopathogenic fungi.

17. A method for treating seed, seed of transgenic plants or transgenic plants comprising contacting the composition of claim 6 with said seed, seed of transgenic plants or transgenic plants.

18. Seed treated with composition according to claim 6.

19. A method for the selective control of harmful plants in crops of useful plants, which comprises applying an effective plant-protecting amount of the composition according to claim 6, where the compounds of formula (I) is applied before, after or simultaneously with an effective amount of said biological control agent to the plants, parts of plants, plant seeds or the seed.

* * * * *